United States Patent [19]

Sung

[11] 4,445,907
[45] May 1, 1984

[54] ALCOHOL COMPOSITION STABILIZED AGAINST CORROSION BY THE USE OF AN AMINO TETRAZOLE

[75] Inventor: Rodney L. Sung, Fishkill, N.Y.

[73] Assignee: Texaco Inc., White Plains, N.Y.

[21] Appl. No.: 206,813

[22] Filed: Nov. 14, 1980

[51] Int. Cl.³ ............................................. C10L 1/22
[52] U.S. Cl. .......................................... 44/53; 44/63; 252/390; 252/392
[58] Field of Search ................ 548/251; 252/390, 392; 44/53, 63

[56] References Cited

U.S. PATENT DOCUMENTS 3,824,249  7/1974  Regnier et al. ..................... 548/251

Primary Examiner—Charles F. Warren
Assistant Examiner—Mrs. Y. Harris-Smith
Attorney, Agent, or Firm—Carl G. Ries; Robert A. Kulason; Carl G. Seutter

[57] ABSTRACT

Alcohols may be inhibited against corrosion by addition there to of an amide reaction product of (i)

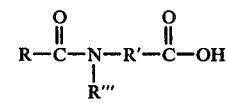

(preferably in the form of the acid, acid chloride or ester) and (ii) an amino tetrazole.

24 Claims, No Drawings

ALCOHOL COMPOSITION STABILIZED AGAINST CORROSION BY THE USE OF AN AMINO TETRAZOLE

FIELD OF THE INVENTION

This invention relates to alcohol products particularly characterized by decreased ability to corrode metal surfaces with which they come into contact.

BACKGROUND OF THE INVENTION

As is well known to those skilled in the art, alcohols such as ethanol may corrode metal surfaces with which they come into contact. This is particularly true of crude or commercially available ethanols which undesirably contain acidic components commonly acetic acid. In the case of fermentation alcohols, acetic acid may be present in amount of 0.003 w %–0.005 w % of the alcohol; and this may be responsible for the fact that the alcohol causes serious corrosion problems.

It is an object of this invention to provide a novel process for decreasing the corrosion of alcohol compositions. Other objects will be apparent to those skilled in the art.

STATEMENT OF THE INVENTION

In accordance with certain of its aspects, the novel composition of this invention may comprise (i) a water-soluble alcohol preferably selected from the group consisting of ethanol and methanol; and (ii) an effective corrosion-inhibiting amount of

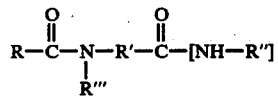

wherein R is a $C_{10}$–$C_{20}$ alkyl, alkenyl, alkaryl, aralkyl, aryl, or cycloalkyl hydrocarbon group, R' is a divalent hydrocarbon group selected from the same group as R and having one less hydrogen, R''' is alkyl, aryl, alkaryl, or aralkyl, and NH—R'' is an amino tetrazole group.

DESCRIPTION OF THE INVENTION

The alcohol compositions which may be treated by the process of this invention may include $C_1$–$C_{12}$ alkanols such as water-soluble alkanols including $C_1$–$C_4$ alcohols. Preferably the alcohols include methanol, ethanol, propanols, etc. The alcohols may include mixtures of alcohols with each other and/or with other compositions including lactones, esters, hydrocarbons, etc. The alcohol may be in the form of gasohol—a mixture commonly containing 80 v %–95 v %, say 90 v % gasoline and 5 v %–20 v %, say 10 v % alcohol. The alcohol may contain water, for example up to 10 w %–20 w %, typically 5 w %; but preferably it will be anhydrous. Anhydrous compositions commonly contain less than about 0.3 v % water, typically 0.001 v %–0.005 v %, say about 0.004 v % water. One preferred charge may be 100% anhydrous ethanol. Another preferred charge may be 100% anhydrous methanol.

Commercially available mixtures may be employed. Illustrative of one such commercially available mixture may be that having the following analysis:

TABLE I

| Component | Parts |
|---|---|
| ethanol | 3157.2 |
| methyl isobutyl ketone | 126.3 |
| acetic acid | 0.256 |
| methyl alcohol | 0.24 |
| isopropyl alcohol | 0.2 |
| n-propyl alcohol | 0.162 |
| ethyl acetate | 0.2 |

It is a particular feature of the process of this invention that it may be used to treat such compositions when they are to be used as fuels, whether the fuel be 100% alcohol or mixtures thereof with one another or with other components. The fuels which may be treated by the process of this invention include gasohols which may be formed by mixing 90–95 volumes of gasoline with 5–10 volumes of ethanol or methanol. A typical gasohol may contain 90 volumes of gasoline and 10 volumes of absolute ethanol.

The fuels to be treated by the process of this invention may be substantially anhydrous, i.e. they contain less than about 0.3 v % water; typically they may contain 0.001 v %–0.005 v %, say about 004 v % water.

It is a feature of these fuels that they may undesirably contain acidic contaminants which may cause serious corrosion problems. These contaminants are particularly in evidence when the alcohol is a commercially available alcohol which contains therein inter alia acids concurrently produced as by fermentation processes for producing ethanol or acids which have been picked up during handling. Acetic acid is a common acid present in the commercially available alcohols produced by fermentation; and it may be present in amount of 0.003 w %–0.005 w % of the total of the alcohol.

In accordance with practice of the process of this invention, there may be added to the alcohol a minor effective corrosion-inhibiting amount of, as a corrosion inhibiting agent, $$R-\overset{\overset{O}{\|}}{C}-\underset{\underset{R'''}{|}}{N}-R'-\overset{\overset{O}{\|}}{C}-[NH-R'']$$

wherein R is a $C_{10}$–$C_{20}$ alkyl, alkenyl, alkaryl, aralkyl, aryl, or cycloalkyl hydrocarbon group, R' is a divalent hydrocarbon group selected from the same group as R and having one less hydrogen, R''' is alkyl, aryl, alkaryl, or aralkyl, and NH—R'' is an amino tetrazole group.

The amides of this invention may be formed by various routes from the acid (or its equivalent, for this purpose, the ester, anhydride or halide)

$$R-\overset{\overset{O}{\|}}{C}-\underset{\underset{R'''}{|}}{N}-R'-\overset{\overset{O}{\|}}{C}-OH$$

In the above compound, R may be a hydrocarbon group, including inertly substituted hydrocarbon groups, selected from the group consisting of alkyl, aralkyl, cycloalkyl, aryl, alkaryl, and alkenyl including such radicals when inertly substituted. When R is alkyl, it may typically be methyl, ethyl, n-propyl, iso-propyl, n-butyl, i-butyl, sec-butyl, amyl, octyl, decyl, octadecyl, etc. When R is aralkyl, it may typically be benzyl, betaphenylethyl, etc. When R is cycloalkyl, it may typically be cyclohexyl, cycloheptyl, cyclooctyl, 2-methylcyclohephtyl, 3-butylcyclohexyl, 3-methylcyclohexyl, etc. When R is aryl, it may typically be phenyl, naphthyl, etc. When R is alkaryl, it may typically be tolyl, xylyl, etc. When R is alkenyl, it may typically be vinyl, allyl, 1-butenyl, etc. R may be inertly substituted, ie.e. it may bear a non-reactive substituent such as alkyl, aryl, cycloalkyl, ether, etc. Typically inertly substituted R groups may include 3-chloropropyl, 2-ethoxyethyl, carboethoxymethyl, 4-methyl cyclohexyl, etc. The preferred R groups may be alkyl groups containing 10–20 carbon atoms including e.g. stearyl (18 carbons), decyl, (10 carbons), and cocoyl (12–18 carbons).

R' may be selected from the same group and have one less hydrogen. Preferably R' is a straight chain lower alkyl group containing 1–5, more preferably 1–3, say 1 carbon atom.

R''' may be an alkyl, aryl, alkaryl, or aralkyl group—which may be selected from the same groups as that from which R is selected. The preferred R''' group is methyl.

Although the amide may be prepared from the acid, the anhydride, or the ester, it is preferred to prepare it from the halide—most preferably the chloride.

The preferred "acids" include acid chlorides wherein R is stearyl, oleyl, or cocoyl and R' is methylene. Typical compounds which may be employed include:

TABLE

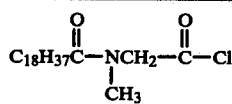

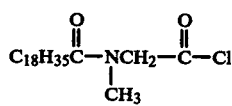

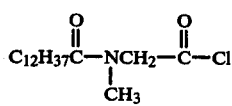

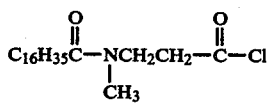

The preferred composition is the compound wherein R is cocoyl, i.e. the commercial mixture of fatty acid residues corresponding to 12–18 carbon atoms.

The amino tetrazoles which may be employed include 1-amino tetrazoles (I), 2-amino tetrazoles (II), 3-amino tetrazoles (III), 4-amino tetrazoles (IV), and 5-amino tetrazoles (V), including those bearing inert substituents which do not interfere with or react in the instant reaction—typified by hydrocarbon or alkoxy groups.

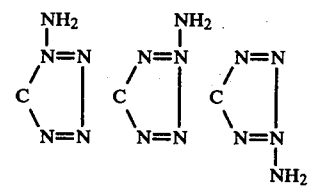

(I)　(II)　(III)

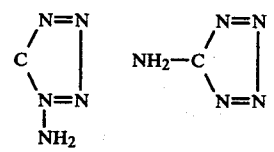

(IV)　(V)

The preferred amino tetrazole may be 5-amino tetrazole.

It will be apparent to those skilled in the art that the several reactants may bear inert substituents typified by alkyl, alkoxy, etc. It will also be apparent that the preferred compounds to be employed will be those which are soluble in the solvents employed during the reaction and which produce products which are soluble in or compatible with the system in which the product is to be employed.

Typical solvents which may be employed may include alcohols as methanol, ethanol, butanols, cyclohexanol, etc. or hydrocarbons including heptane, octane, toluene, xylene, gasoline, etc. It is preferred that the solvent system include alcohol and hydrocarbon. A particularly preferred system may include equal volumes of methanol and xylene.

Formation of the desired additive may preferably be effected by placing the amino tetrazole in a reaction vessel in an excess of solvent. A typical solvent (e.g. equal volumes of methanol and xylene) may be present in an excess amount of typically 50–200 volumes, say 120 volumes per volume of the total of the other reactants. The acid (in preferably equimolar amount) may be added slowly with agitation to the reaction mixture. It is not necessary to add catalyst.

As the acid is added, the following typical reaction occurs (in the case of 5-amino-1-H-tetrazole).

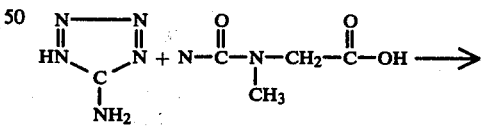

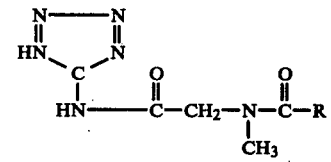

wherein R may preferably be a $C_{12}$–$C_{18}$ alkyl such as oleoyl or tallowyl or cocoyl.

During and after addition of the acid or acid chloride, the reaction mixture may be refluxed at 50° C.–80° C., say 76° C. for 1–10 hours, say 3 hours. At the end of the reaction period the reaction mixture may be cooled to ambient temperature of 20° C.–27° C., say 25° C. and filtered and then stripped (as by distillation at 80° C.–100° C., say 76° C.) of solvent. When the acid chloride is used, a base (hydrogen halide acceptor) such as puridine, triethylamine, sodium hydroxide, potassium hydroxide, etc. is used to remove the hydrogen chloride which is produced as by-product.

The residue which is generally a waxy solid or viscous liquid is recovered in yield approaching stoichiometric.

The so-prepared rust and corrosion inhibitors may be added to alcohols or to antifreeze. These compositions may be particularly found to be effective as rust and corrosion inhibitors when added to alcohols typified by those available commercially containing compounds including ethers, esters, acids, etc. and also including absolute alcohols, alcohols containing water such as 95 w % ethanol, gasohols, etc.

The so-prepared rust and corrosion inhibitors may be added to alcohol in amount of 0.25–25 PTB, preferably 1–20 PTB, more preferably 1–10 PTB, say 10 PTB. (PTB stands for pounds of additive per thousand barrels of alcohol.) Alternatively expressed, the inhibitor may be added to an alcohol in minor corrosion-inhibiting amount of 0.0001–0.01 w % preferably 0.0004–0.008 w %, more preferably 0.0004–0.004 w %, say 0.004 w %. Larger amounts may be employed but may not be necessary.

It is a feature of this invention that the alcohol composition so prepared is characterized by its increased corrosion and rust inhibition, i.e. its decreased ability to form rust on iron surfaces in the presence of aqueous acid systems.

The corrosive nature of the formulated products may be readily measured by the Iron Strip Corrosion Test (ISCT). In this test, an iron strip (12 mm×125 mm±1 mm) is prepared by washing in dilute aqueous hydrochloric acid to remove mill scale, then with distilled water to remove the acid, then with acetone followed by air drying. The strip is then polished with #100 emery cloth.

The polished strip is totally immersed in 110 ml of the test liquid in a 4 ounce bottle for 15 minutes at room temperature of 20° C. 20 ml of the test liquid is poured off and replaced with 10 ml of distilled water. The bottle is shaken and the sample is maintained for 3 hours at 90° F. The percent rust on the strip is determined visually. A second reading may be taken after 40 hours and another after 6 days.

The inhibited alcohols of this invention, after 6 days of ISCT, generally show a Rust and Corrosion rating below about 2–3% and frequently as low as trace-to-1%.

DESCRIPTION OF PREFERRED EMBODIMENTS

Practice of this invention will be apparent to those skilled in the art from the following examples wherein, as elsewhere in this specification, all parts are parts by weight unless otherwise specified.

EXAMPLE I

In this example which illustrates the best mode known to me of practicing the process of this invention, there is added to a reaction vessel 175 parts of the Sarkosyl LC brand of cocoyl sarcosine having the formula $$R-\underset{\underset{CH_3}{|}}{C(=O)-N}-CH_2-C(=O)-OH$$

wherein R, the cocoyl radical, is a mixture of saturated straight chain alkyl group having 12–18 carbon atoms. There is also added 42.5 parts of 5-amino tetrazole and 4 parts of crystallite, a hydrocarbon solvent having a boiling range of 300° F.–550° F.

The mixture is refluxed for 3 hours at 175° C. during which time 8 parts of water are recovered. The reaction mixture is cooled, filtered, and stripped of crystallite solvent. The product is characterized by infra-red spectra and by NMR.

EXAMPLE II

In this example, the reaction product of Example I (20 PTB of additive) is added to 90 parts of the ethanol of Table I.

Distilled water (10 parts) is added and the system is subjected to the ISCT Test. The iron strip is observed after 6 days.

EXAMPLE III

In this control Example, the system of Example II is tested without the additive.

EXAMPLE IV

In this control Example, the procedure of Example II is employed except that the additive is a prior art commercial rust and corrosion inhibitor (100 PTB) and only 3 parts of distilled water are added. The additive is the Ethomid HT/15 brand of polyoxyethylene (5) hydrogenated tallow amide.

The results of the Iron Strip Corrosion Test were as follows:

TABLE

| Example | Six-Day Rust & Corrosion Rating |
|---|---|
| II | 1%–5% |
| III | 30% |
| IV | 25% |

From the above Table, it will be apparent that the system of Example II, prepared in accordance with practice of the process of this invention, showed 1%–5% rust and corrosion. Control Examples III–IV showed 25%–30% rust and corrosion which is unsatisfactory.

Results comparable to those of Example I may be obtained when the acid reacted is:

TABLE

| Example | Acid |
|---|---|
| V | $\text{Stearyl-}\underset{}{C(=O)}-\underset{\underset{CH_3}{|}}{N}-CH_2-C(=O)-OH$ |
| VI | $\text{Lauryl-}\underset{}{C(=O)}-\underset{\underset{CH_3}{|}}{N}-CH_2-C(=O)-OH$ |

TABLE-continued

| Example | Acid |
|---|---|
| VII | 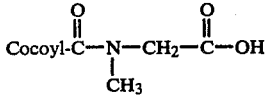 |

Results comparable to those of Examples I and II may be obtained when the amino tetrazole reactant is:

TABLE

| Example | Amino Tetrazole |
|---|---|
| VIII | 1-amino tetrazole |
| IX | 2-amino tetrazole |
| X | 3-amino tetrazole |
| XI | 4-amino tetrazole |

Results comparable to those of Example I and II may be obtained if the fuel is as follows:

TABLE

| Example | Fuel |
|---|---|
| XII | Gasoline containing 90 v % gasoline and 10 v % absolute ethanol |
| XIII | absolute ethanol |
| XIV | absolute methanol |

Although this invention has been illustrated by reference to specific embodiments, it will be apparent to those skilled in the art that various changes and modifications may be made which clearly fall within the scope of this invention.

What is claimed is:

1. A composition comprising
   (i) a water-soluble alcohol; and
   (ii) an effective corrosion-inhibiting amount of

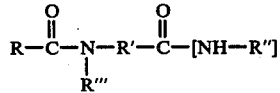

wherein R is a $C_{10}$-$C_{20}$ alkyl, alkeny, alkaryl, aralkyl, aryl, or cycloalkyl hydrocarbon group, R' is a divalent $C_1$-$C_5$ lower alkylene hydrocarbon group, R''' is alkyl, aryl, alkaryl, or aralkyl, and NH—R'' is an amino tetrazole group.

2. A composition as claimed in claim 1 wherein said alcohol is ethanol.
3. A composition as claimed in claim 1 wherein said alcohol is methanol.
4. A composition as claimed in claim 1 wherein said alcohol contains $C_1$-$C_4$ alcohol.
5. A composition as claimed in claim 1 wherein R is an alkyl group.
6. A composition as claimed in claim 1 wherein R is stearyl.
7. A composition as claimed in claim 1 wherein R is decyl.
8. A composition as claimed in claim 1 wherein R is cocoyl.
9. A composition as claimed in claim 1 wherein R' is a straight chain $C_1$-$C_5$ alkyl group.
10. A composition as claimed in claim 1 wherein R' is —$CH_2$—.
11. A composition as claimed in claim 1 wherein R is cocoyl and R' is —$CH_2$—.
12. A composition as claimed in claim 1 wherein R'' is derived from 5-amino tetrazole.
13. A composition as claimed in claim 1 wherein said effective corrosion-inhibiting amount is 0.25-25 pounds per thousand barrels of composition.
14. A composition comprising
   (i) a water-soluble alcohol; and
   (ii) an effective corrosion-inhibiting amount of

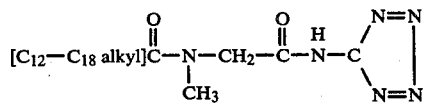

15. A composition comprising

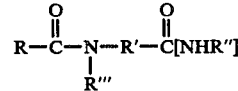

wherein R is a $C_{10}$-$C_{20}$ alkyl, alkenyl, alkaryl, aralkyl, aryl, or cycloalkyl hydrocarbon group, R' is a divalent $C_1$-$C_5$ lower alkylene hydrocarbon group, R''' is alkyl, aryl, alkaryl, or aralkyl, and NH—R'' is an amino tetrazole group.

16. A composition as claimed in claim 15 wherein R is an alkyl group.
17. A composition as claimed in claim 15 wherein R is stearyl.
18. A composition as claimed in claim 15 wherein R is decyl.
19. A composition as claimed in claim 15 wherein R is cocoyl.
20. A composition as claimed in claim 15 wherein R is a straight chain $C_1$-$C_5$ alkyl group.
21. A composition as claimed in claim 15 wherein R' is —$CH_2$—.
22. A composition as claimed in claim 15 wherein R is cocoyl and R' is —$CH_2$—.
23. A composition as claimed in claim 15 wherein R'' is derived from 5-amino tetrazole.
24.

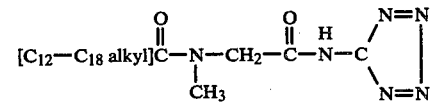

* * * * *